(12) United States Patent  
Kim et al.

(10) Patent No.: US 9,155,477 B2
(45) Date of Patent: Oct. 13, 2015

(54) PRESSURIZING APPARATUS

(75) Inventors: Jong Pal Kim, Seoul (KR); Kun-soo Shin, Seongnam-si (KR); Sang-kon Bae, Seongnam-si (KR); Youn-ho Kim, Hwaseong-si (KR)

(73) Assignee: SAMSUNG ELECTRONICS CO., LTD. (KR)

( * ) Notice: Subject to any disclaimer, the term of this patent is extended or adjusted under 35 U.S.C. 154(b) by 953 days.

(21) Appl. No.: 12/607,484

(22) Filed: Oct. 28, 2009

(65) Prior Publication Data

US 2010/0185104 A1  Jul. 22, 2010

(30) Foreign Application Priority Data

Jan. 19, 2009 (KR) .................. 10-2009-0004197

(51) Int. Cl.
*A61B 5/02* (2006.01)
*A61B 5/022* (2006.01)

(52) U.S. Cl.
CPC ................. *A61B 5/02233* (2013.01)

(58) Field of Classification Search
CPC .... A61B 5/022; A61B 5/02233; A61B 5/021; A61B 5/681
USPC ............ 600/485–507; 73/700, 866.5; 269/55, 269/57–58
See application file for complete search history.

(56) References Cited

U.S. PATENT DOCUMENTS

| | | | | |
|---|---|---|---|---|
| 4,206,765 A * | 6/1980 | Huber | ........................... | 600/490 |
| 4,830,017 A * | 5/1989 | Perry et al. | .................... | 600/485 |
| 5,240,007 A * | 8/1993 | Pytel et al. | ..................... | 600/485 |
| 5,271,405 A * | 12/1993 | Boyer et al. | ................... | 600/485 |
| 5,722,414 A * | 3/1998 | Archibald et al. | ............ | 600/485 |
| 5,769,290 A * | 6/1998 | Pestana | ......................... | 224/178 |
| 5,908,027 A * | 6/1999 | Butterfield et al. | ........... | 600/485 |
| 6,159,157 A * | 12/2000 | Archibald et al. | ............ | 600/485 |
| 6,837,858 B2 * | 1/2005 | Cunningham et al. | ........ | 600/573 |
| 2002/0079792 A1 * | 6/2002 | Nott et al. | ...................... | 312/248 |
| 2006/0079792 A1 * | 4/2006 | Finburgh et al. | .............. | 600/485 |
| 2008/0132795 A1 | 6/2008 | Ghigini | | |

FOREIGN PATENT DOCUMENTS

| | | |
|---|---|---|
| JP | 11318835 A | 11/1999 |
| JP | 2000000140 A | 1/2000 |
| JP | 2003144398 A | 5/2003 |
| JP | 2005334124 A | 12/2005 |
| JP | 2008063852 A | 3/2008 |
| JP | 2008068471 A | 3/2008 |
| KR | 1020060046487 A | 5/2006 |

* cited by examiner

*Primary Examiner* — Navin Natnithithadha
*Assistant Examiner* — Eric Messersmith
(74) *Attorney, Agent, or Firm* — Cantor Colburn LLP

(57) ABSTRACT

A pressurizing apparatus includes a lower frame and an upper frame. A first end of the upper frame may be hinged to the lower frame at a rotation axis, and a second end of the upper frame may be rotated about the rotation axis by an actuator. A pressurizing unit may be combined to the upper frame in such a way that the pressurizing unit is rotatable relative to the upper frame. When the actuator rotates the second end of the upper frame, the pressurizing unit pressurizes an object to be pressurized.

18 Claims, 5 Drawing Sheets

PRESSURIZING APPARATUS

CROSS-REFERENCE TO RELATED APPLICATIONS

This application claims priority to Korean Patent Application No. 10-2009-0004197, filed on Jan. 19, 2009, and all the benefits accruing therefrom under 35 U.S.C. §119, the disclosure of which is incorporated herein in its entirety by reference.

BACKGROUND

1. Field

One or more embodiments relate to a pressurizing apparatus used in an apparatus for measuring blood pressure.

2. Description of the Related Art

A pressurizing apparatus, which pressurizes a radial artery of a wrist with an air bag, when wrapped around the wrist, is used in an apparatus for measuring blood pressure. The air bag, installed in a frame of such a pressurizing apparatus, is closely adhered to and pressurizes a radial artery area of the wrist by using a motor and a string. Thus, blood pressure is measured by detecting a pressure change inside the air bag due to a pulse wave of the radial artery.

As described above, the pressurizing apparatus includes a frame, an air bag and a motor installed in the frame, a wristband having one end connected to the frame, and a string that connects the motor and the other end of the wristband. The wristband is wrapped around and fixed around a wrist, and the string is pulled by driving the motor. Accordingly, the wristband tightens around the wrist, and the air bag pressurizes a radial artery area of the wrist.

However in the pressurizing apparatus, when the wristband is placed around the wrist, the air bag is pressed by tension of the wristband, and thus, a predetermined pre-pressure is applied to the air bag. Here, the pre-pressure applied to the air bag differs whenever the wristband is placed on the wrist. When the pre-pressure is equal to or above about 50 millimeters of mercury (mmHg), blood pressure during a relaxation period is unable to be measured, or a measured value thereof is unreliable.

Also, in the pressurizing apparatus, the air bag is placed on the radial artery area of the wrist, and then fixed by tightening the wristband. Here, due to the connection of the air bag with the frame, the air bag may be warped since the air bag is easily deformable. When the air bag is pressurized while being warped, the air bag may remarkably slant to one side, and thus, it may be difficult to normally pressurize the wrist and measure blood pressure.

Moreover, in the pressurizing apparatus, a large motor is used to generate suitable pressure, and thus, it is difficult to minimize the pressurizing apparatus.

SUMMARY

One or more embodiments include a pressurizing apparatus used in an apparatus for measuring blood pressure.

Exemplary embodiments will be set forth in part in the description which follows and, in part, will be apparent from the description, or may be learned by practice of the illustrated embodiments.

One or more embodiments may include a pressurizing apparatus including a lower frame, an upper frame including one end hinged to the lower frame, an actuator rotating the other end of the upper frame, and a mounting unit for mounting the lower frame to an object to be pressurized by being connected to the lower frame. The object is pressurized when the actuator rotates the other end of the upper frame toward the object.

The pressurizing apparatus may further include a pressurizing unit installed to be rotatable in the upper frame. The pressurizing unit pressurizes the object by contacting the object according to the rotation of the other end of the upper frame.

The pressurizing unit may be a fluid bag containing a fluid. The fluid bag may include a body, an upper fixing frame combined to an upper portion of the body, a lower fixing frame combined to a lower portion of the body, and a rotation shaft combined to the upper frame such that the rotation shaft protrudes from each side of the upper fixing frame.

The upper frame may have a rectangular frame shape including a hollow portion, and the pressurizing unit may be disposed inside the hollow portion.

A rotation center of the pressurizing unit may be disposed on a location that is offset by a predetermined interval from a center axis of the pressurizing unit toward the one end of the upper frame.

A rotation shaft may be disposed to protrude from each of two sides of the pressurizing unit, and a groove to which the rotation shaft is inserted may be disposed in the upper frame.

The lower frame may include a mounting part to which the actuator is mounted, and two arms that are parallel and extend from the mounting part. The upper frame may be disposed between the two arms, and distal ends of the arms may be hinged to the one end of the upper frame.

A hinge shaft may be installed to the ends of the arms and a groove to which the hinge shaft is inserted may be disposed in the one end of the upper frame. A combining shaft for combining the mounting unit to the mounting part may be installed in the mounting part.

A spring may be installed between the lower frame and the upper frame. The spring may apply elasticity to the upper frame in a direction, where the other end of the upper frame is distanced away from the lower frame.

The actuator may include a driving motor mounted on the lower frame, and a string connecting the driving motor and the other end of the upper frame.

A pulley may be installed on a rotation shaft of the driving motor, and the string may be wrapped around the pulley. An end of the string may be fixed to the lower frame via supporting members disposed on the other end of the upper frame. The supporting members may include two supporting rollers spaced apart from each other. A guide roller for maintaining a direction of the string may be installed in the lower frame.

The mounting unit may include a mounting band. Both of two ends of the mounting band may be each connected to both of two ends of the lower frame, respectively. An adhesion unit may be prepared in a center of the mounting band. The mounting unit may further include a mounting frame surrounding at least a part of the object, and the lower frame may be combined to the mounting frame.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Figure 1:
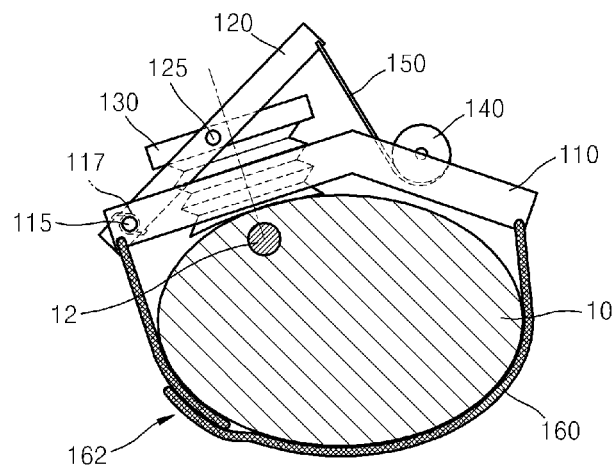
FIG. 1 is a cross-sectional view schematically illustrating an exemplary embodiment of a pressurizing apparatus according to the invention.

Reference will now be made in detail to embodiments, examples of which are illustrated in the accompanying drawings, wherein like reference numerals refer to the like elements throughout. In this regard, the illustrated embodiments may have different forms and should not be construed as being limited to the descriptions set forth herein. Accordingly, the embodiments are merely described below, by referring to the figures, to explain features of the invention.

It will be understood that when an element or layer is referred to as being "on", "connected to" or "coupled to" another element or layer, the element or layer can be directly on, connected or coupled to another element or layer or intervening elements or layers. In contrast, when an element is referred to as being "directly on," "directly connected to" or "directly coupled to" another element or layer, there are no intervening elements or layers present. As used herein, connected may refer to elements being physically and/or electrically connected to each other.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the invention.

Spatially relative terms, such as "below", "lower", "under," "above", "upper" and the like, may be used herein for ease of description to describe the relationship of one element or feature to another element(s) or feature(s) as illustrated in the figures. It will be understood that the spatially relative terms are intended to encompass different orientations of the device in use or operation, in addition to the orientation depicted in the figures. For example, if the device in the figures is turned over, elements described as "below" or "lower" relative to other elements or features would then be oriented "above" relative to the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the invention are described herein with reference to cross-section illustrations that are schematic illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

Hereinafter, the invention will be described in detail with reference to the accompanying drawings.

Figure 2:
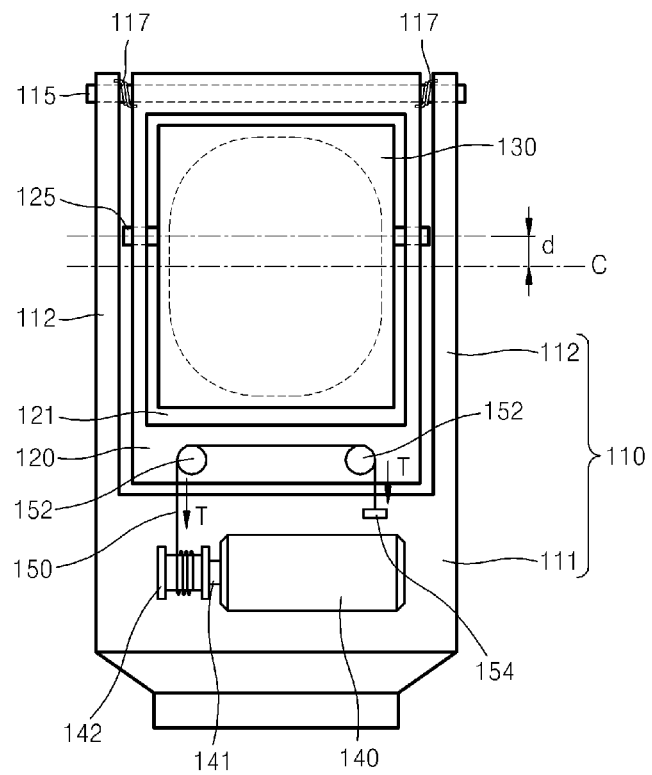
FIG. 2 is a plan view schematically illustrating the pressurizing apparatus illustrated in FIG. 1.

FIG. 1 is a cross-sectional view schematically illustrating an exemplary embodiment of a pressurizing apparatus according to the invention, and FIG. 2 is a plan view schematically illustrating the pressurizing apparatus illustrated in FIG. 1.

Referring to FIGS. 1 and 2, the pressurizing apparatus according to the illustrated embodiment includes a lower frame 110, an upper frame 120 including a first end hinged to the lower frame 110, an actuator rotating a second end of the upper frame 120 opposite to the first end, and a mounting unit for mounting the lower frame 110 to an object to be pressurized, by being connected to the lower frame 110. The lower frame 110 and/or the upper frame 120 is a single unitary and indivisible member.

The lower frame 110 supports configuration elements of the pressurizing apparatus, and includes a mounting part 111 to which the actuator is mounted, and two arms 112 that are parallel to each other and extend from the mounting part 111. The upper frame 120 is disposed between the two arms 122, and distal ends of the two arms 122 are hinged to the first end of the upper frame 120, such that the lower frame 110 and the upper frame 120 are movable relative to each other about a rotation axis of the hinge structure.

Figure 4:
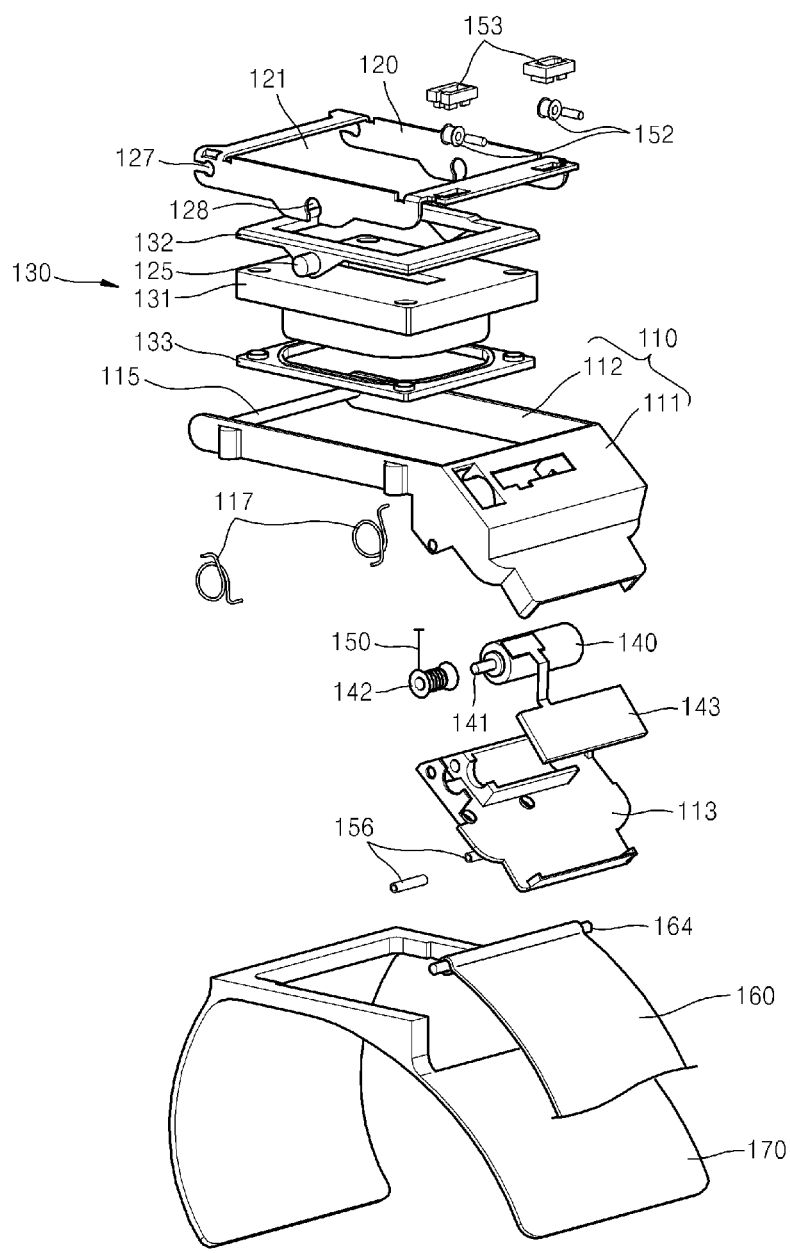
FIG. 4 is an exploded perspective view illustrating a detailed structure of an alternative exemplary embodiment of the pressurizing apparatus illustrated in FIGS. 1 and 2.

A hinge shaft 115 is installed to the distal ends of the two arms 122, and a groove 127 of FIG. 4 to which the hinge shaft 115 is inserted, may be disposed in the end of the upper frame 120. The upper frame 120 is pivotable relative to the lower frame 110 about a pivot axis, such as defined by a longitudinal extension direction of the hinge shaft 115. The hinge shaft 115, the arms 122 and the mounting part 111 collectively and solely define an enclosed opening of the lower frame 110.

The upper frame 120 has a rectangular frame shape including a hollow portion 121. As described above, the first end of the upper frame 120 is hinged to the lower frame 110, and the second end of the upper frame 120 is able to rotate in a predetermined angle about the hinge shaft 115. The hollow portion 121 is considered an enclosed opening which is solely defined by sidewalls of the substantially frame-shaped upper frame 120. The hollow portion 121 of the upper frame 120 is aligned with the enclosed opening of the lower frame 110.

A spring 117 may be installed disposed on a portion of the hinge shaft 115 between the lower frame 110 and the upper frame 120, as best shown in FIG. 2. The spring 117 applies elasticity on the upper frame 120 in a direction where the second end of the upper frame 120 is distanced away from the lower frame 110. In one exemplary embodiment, the spring 117 may be a torsion spring installed on the hinge shaft 115.

A pressurizing unit, which pressurizes an object to be pressurized by contacting the object, may be installed on the upper frame 120. The pressurizing unit contacts the object, for example, a wrist 10, so as to pressurize a radial artery 12 of the wrist 10. The pressurizing unit may include a flexible or deformable fluid bag 130 containing a fluid, such as air.

The fluid bag 130 is disposed in the hollow portion 121 of the upper frame 120, and is combined to the upper frame 120 in such a way that the fluid bag 130 may rotate in a predetermined angle. In the illustrated embodiment, the fluid bag 130 and the upper frame 120 may be combined with each other via a rotation shaft 125, such that the fluid bag 130 may rotate in a predetermined angle about the rotation shaft 125. In an alternative embodiment, a contact sensor may be used as the pressurizing unit, instead of the fluid bag 130.

The actuator pressurizes the object by rotating the second end of the upper frame 120 toward the object. The actuator may include a driving motor 140 and a string 150. The string 150 is a single unitary indivisible unit. The driving motor 140 is mounted in the mounting part 111 of the lower frame 110, and provides a driving power for moving the second end of the upper frame 120 towards the object.

In the illustrated embodiment, a pulley 142 may be installed on a rotation shaft 141 of the driving motor 140, and the pulley 142 of the driving motor 140 and the second end of the upper frame 120 may be connected by the string 150. When the string 150 is pulled as the driving motor 140 is driven, the second end of the upper frame 120 rotates in a predetermined angle around the hinge shaft 115, thereby pressurizing the fluid bag 130.

When the driving motor 140 is not driven, the string 150 is maintained in a loose state, and thus, the fluid bag 130 is not pressurized. Here, as described above, when the spring 117 is installed between the lower frame 110 and the upper frame 120, the second end of the upper frame 120 is biased to be positioned distanced away from the lower frame 110 by the spring 117.

The pressurizing unit mounts and fixes the lower frame 110 to the object, such as the wrist 10. The pressurizing unit may include a mounting band 160 connected to the lower frame 110. A first end and a second end opposing the first end of the mounting band 160, are connected to a first end and a second end opposing the first end of the lower frame 110, respectively. The mounting band 162 may be a single continuous indivisible member, or the mounting band 162 may include multiple separate portions which are fixed together at distal ends thereof by an adhesion unit 162. The adhesion unit 162 together with the lower frame 110 may effectively enclose the object, as illustrated in FIG. 1. In an exemplary embodiment, the adhesion unit 162 may be provided in a center of the mounting band 160.

In the pressurizing apparatus including a structure as described above, when the string 150, connecting the upper frame 120 and the driving motor 140, is maintained loose while mounting the pressurizing apparatus to the wrist 10, the tension of the mounting band 160 is not applied to the fluid bag 130 even when the mounting band 160 is strongly tightened to enclose the wrist 10. In other words, the mounting band 160 is only used to mount the pressurizing apparatus to the wrist 10, and is not used to pressurize the fluid bag 130. Accordingly, when the pressurizing apparatus is mounted on the wrist 10, pre-pressure due to the tension of the mounting band 160 is not applied to the fluid bag 130.

A first end of the string 150 is wrapped around the pulley 142 of the driving motor 140, and a second end of the string 150 opposite the first end, may be fixed to a static fixing member 154 disposed in the lower frame 110. The continuous string 150 member is disposed bent around and contacting two supporting members 152 spaced apart from each other on the second end of the upper frame 120. In other words, the string 150 may be connected to each of the two supporting members 152 of the upper frame 120, the driving motor 140, and the fixing member 154 of the lower frame 110. According to such a structure, tension T (indicated by an arrow in FIG. 2) is applied to the string 150 between a first supporting member 152 and the driving motor 140, and between a second supporting member 152 and the lower frame 110 according to the pulley principle, and thus, force applied to the upper frame 120 is twice the force of the driving motor 140.

Also, when force is applied to the second end of the upper frame 120 by the driving motor 140 and the string 150, the first end of the upper frame 120 rotates about the hinge shaft 115, and thus, pressure is applied to the fluid bag 130. Here, since the lever principle is applied, pressure applied to the fluid bag 130 is greater than driving power of the driving motor 140.

As described above, the pressurizing apparatus according to the illustrated embodiment includes a device that amplifies the driving power of the driving motor 140 according to the pulley principle and the lever principle, and accordingly, an overall size of the pressurizing apparatus is minimized since a small driving motor 140 may be used.

Figure 3:
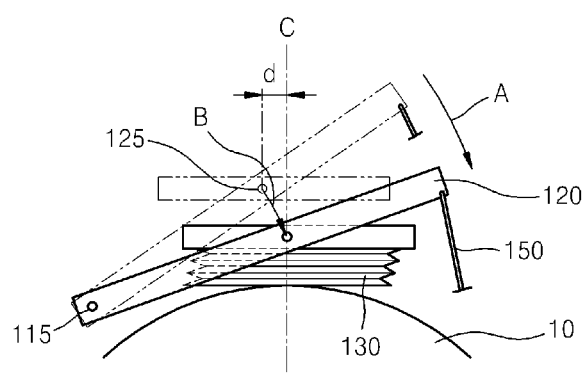
FIG. 3 is a diagram for describing an exemplary embodiment of a motion of a rotation shaft and deformation of a fluid bag according to a rotation of an upper frame.

FIG. 3 is a diagram for describing an exemplary embodiment of a motion of the rotation shaft 125 and deformation of the fluid bag 130 according to a rotation of the upper frame 120.

Referring to FIG. 3, the upper frame 120 and the fluid bag 130 are movably combined with each other by the rotation shaft 125. When the upper frame 120 rotates in a direction of an arrow A, the rotation shaft 125 moves in a direction of an arrow B. Here, when the rotation shaft 125 is in a location of a center axis C of the fluid bag 130, the rotation shaft 125 moves away from the center axis C if the upper frame 120 rotates in the direction of the arrow A, and thus, the fluid bag 130 tilts towards the direction of the arrow A. Accordingly, normal pressure is not applied on a surface of the wrist 10.

In the illustrated embodiment, the rotation shaft 125 combining the upper frame 120 and the fluid bag 130 may be installed in a location that is offset from the center axis C of the fluid bag 130, by a predetermined interval d in a first direction towards the hinge shaft 115 and away from the second end of the upper frame 120, with respect to the center axis C of the fluid bag 130. As described in FIG. 3, when the upper frame 120 rotates in the direction of the arrow A, the rotation shaft 125 moves to the center axis C of the fluid bag 130. Accordingly, a pressurizing direction is substantially perpendicular to the skin surface of the wrist 10, and thus, warping of the fluid bag 130 is reduced or effectively prevented, and a lower surface of the fluid bag 130 is substantially parallel to the skin surface of the wrist 10. Accordingly, pressure is normally applied to the wrist 10.

FIG. 4 is an exploded perspective view illustrating a detailed structure of an alternative exemplary embodiment of the pressurizing apparatus illustrated in FIGS. 1 and 2.

Referring to FIG. 4, the lower frame 110 includes the mounting part 111 and the two arms 122, and the hinge shaft 115 is combined to the ends of the two arms 122 as described above. The driving motor 140 is mounted in the mounting part 111 of the lower frame 110, and may be covered by a cover 113. The pulley 142 is combined to the rotation shaft 141 of the driving motor 140, and the first end of the string 150 is wrapped around the pulley 142.

Also, a control board 143 for controlling the driving motor 140 may be installed in the mounting part 111. Also, a combining shaft 164 for combining the mounting band 160 to the lower frame 110, and a guide roller 156 for maintaining a direction of the string 150, may be installed in the mounting part 111.

The first end of the upper frame 120 is disposed between the two distal ends of the arms 122 of the lower frame 110, and the first end of the upper frame 120 is hinged to the hinge shaft 115. Accordingly, the groove 127 to which the hinge shaft 115 is inserted may be disposed in the first end of the upper frame 120. Also, the supporting members 152 for supporting the string 150 are installed in the second end of the upper frame 120. The supporting members 152 may be two supporting rollers that are spaced apart from one another. The supporting members 152 may each be covered and fixed by the cover 153.

The fluid bag 130 is disposed in the hollow portion 121 of the upper frame 120, such that the fluid bag 130 extends completely through the enclosed hollow portion 121 of the upper frame 120 and the enclosed opening of the lower frame 110, as illustrated in FIGS. 1 and 3. The fluid bag 130 may include a body 131, an upper fixing frame 132 combined to an upper part of the body 131, and a lower fixing frame 133 combined to a lower part of the body 131. The rotation shaft 125 protrudes along a second direction from both of opposing sides of the upper fixing frame 132, and is inserted to a groove 128 disposed in the upper frame 120. Accordingly, the fluid bag 130 is combined to the upper frame 120 in such a way that the fluid bag 130 is rotatably disposed relative to the upper frame 120 about the rotation shaft 125.

The spring 117 may be installed between portions of the lower frame 110 and the upper frame 120, and may be installed on the hinge shaft 115, such as to bias the upper frame 120 and the fluid bag 120 away from the arms 122 of the lower frame 110.

In the pressurizing apparatus according to an exemplary embodiment, the mounting unit may further include a mounting frame 170, which has a shape that substantially conforms to a profile of the wrist 10 such that the mounting frame effectively surrounds the wrist 10 so as to be easily mounted on the wrist 10. Here, the mounting frame 170 may be combined to the lower frame 110.

Figure 5A:
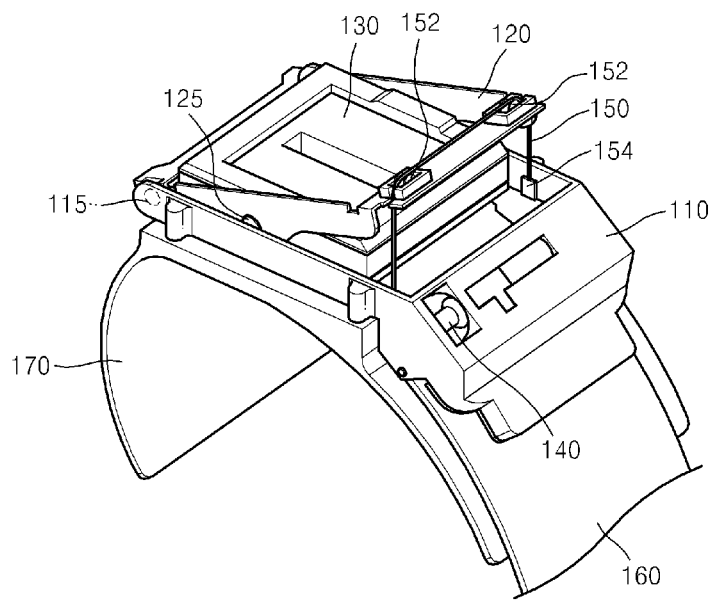
FIGS. 5A and 5B are respectively a perspective view and a side view illustrating the assembled pressurizing apparatus illustrated in FIG. 4 in a state that the fluid bag is not pressurized since a string is loosely maintained.
Figure 5B:
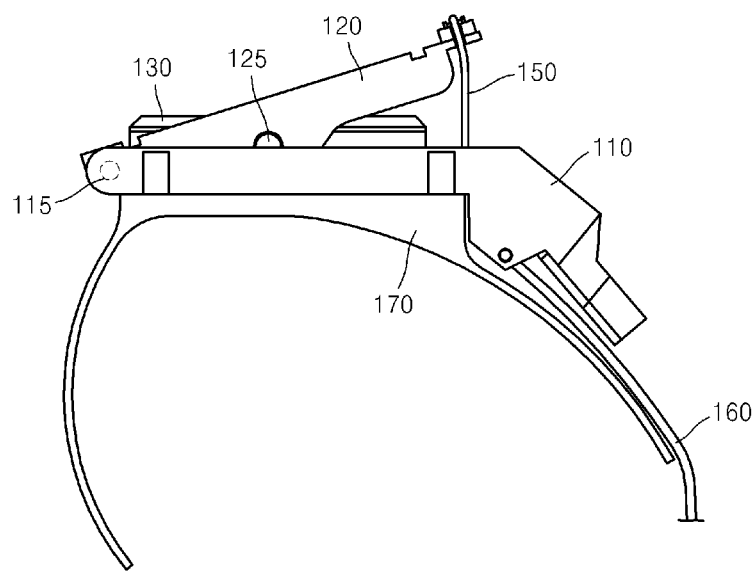

The combining shaft 164 combines a first end of the mounting band 160 to the lower frame 110. A portion of the mounting band 160 extending from the first end, overlaps and extends further than a first portion of the mounting frame 170, as shown in FIGS. 5A and 5B. A second end of the mounting band 160 opposing the first end, may be connected to a second portion of the mounting frame 170 opposing the first portion, such that the mounting band 160 and the mounting frame 170 collectively completely surround the wrist 10.

FIGS. 5A and 5B are respectively a perspective view and a side view illustrating the assembled pressurizing apparatus of FIG. 4 in a state that the fluid bag 130 is not pressurized, since the string 150 is loosely maintained.

Referring to FIGS. 5A and 5B, when the pressurizing apparatus is mounted on the wrist 10 of FIG. 1, the string 150 connecting the upper frame 120 and the driving motor 140 is loosely maintained. Accordingly, even when the pressurizing apparatus is fixed on the wrist 10 by tightening the mounting band 160, the upper frame 120 is distanced away from the lower frame 110 by a predetermined angle, and thus, the fluid bag 130 is not pressurized. The fluid bag 130 may not be protruded from the enclosed opening of the lower frame 110 when the second end of the upper frame 120 is distanced away from the enclosed opening of the lower frame 110. Accordingly, when the pressurizing apparatus is mounted on the wrist 10, pre-pressure is not applied to the fluid bag 130 and the fluid bag 130 is not warped.

Figure 6A:
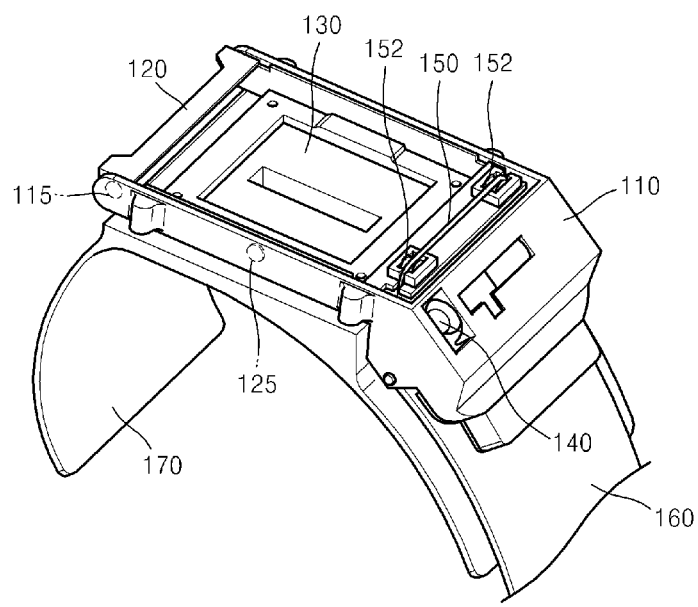
FIGS. 6A and 6B are respectively a perspective view and a side view illustrating the assembled pressurizing apparatus of FIG. 4 in a state that the fluid bag is pressurized since the string is pulled by a driving motor.
Figure 6B:
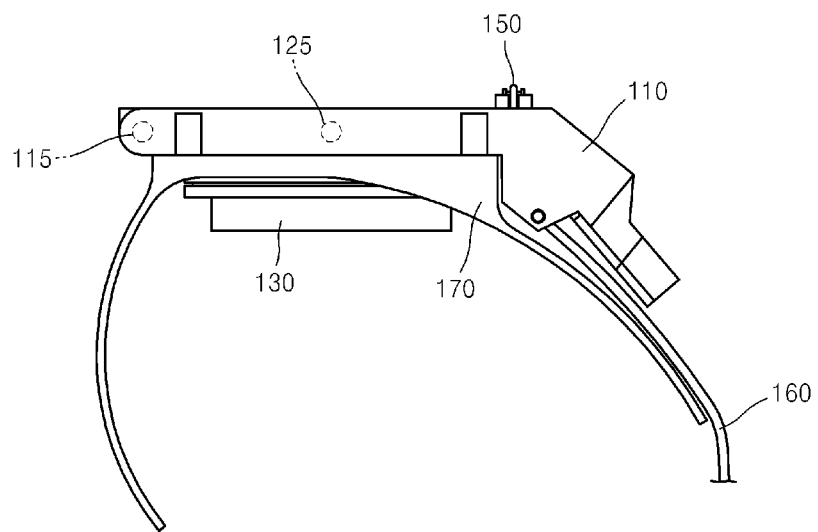

FIGS. 6A and 6B are respectively a perspective view and a side view illustrating the assembled pressurizing apparatus of FIG. 4 in a state that the fluid bag 130 is pressurized since the string 150 is pulled by the driving motor 140.

Referring to FIGS. 6A and 6B, the pressurizing apparatus is fixed on the wrist 10 by tightening the mounting band 160, and then, the string 150 is pulled by driving the driving motor 140. Accordingly, the upper frame 120 rotatably moves about the hinge shaft 115, and thus, the fluid bag 130 moves downward towards the wrist 10. As illustrated in FIG. 3, the fluid bag 130 that moves downward contracts while contacting with and pressurizing the wrist 10. The fluid bag 130 protrudes through both the hollow portion of the upper frame 120 and the enclosed opening of the lower frame 110 to come into contact with an outer surface of the wrist 10.

As described above, sufficient pressure is generated, even by using the small driving motor 140, according to the pulley principle and the lever principle. Also, since the center axis C of the fluid bag 130 and the rotation shaft 125 are offset, warping of the fluid bag 130 is reduced or effectively prevented while being pressurized and contracted. Accordingly, the outer (e.g., skin) surface of the wrist 10 and the lower surface of the fluid bag 130 are maintained substantially parallel and in contact with to each other, and thus, the wrist 10 is normally pressurized.

When the fluid bag 130 pressurizes the wrist 10 while the fluid bag 130 protrudes through both the hollow portion of the upper frame 120 and the enclosed opening of the lower frame 110 to come into contact with an outer surface of the wrist 10, the upper frame 120 is disposed within the enclosed opening of the lower frame 110, and an upper surface of the upper frame 120 is disposed even with (e.g., flush) or below an upper surface of the lower frame 110, as illustrated in the side view of FIG. 6B. The force of the driving motor 140 in combination with the upper frame 120 being pivotable about the hinge shaft 115, retains the fluid bag 130 in contact with and pressurizing the wrist 10, and retains the upper frame 120 disposed between the arms 112 of the lower frame 110.

It should be understood that the exemplary embodiments described therein should be considered in a descriptive sense only and not for purposes of limitation. Descriptions of features within each embodiment should typically be considered as available for other similar features in other embodiments.

What is claimed is:
1. A pressurizing apparatus comprising:
a lower frame;
an upper frame including a first end hinged to a first end of the lower frame, at a first rotation axis, in which is defined a second groove at the first end thereof hinged to the first end of the lower frame;

an actuator connected to a second end of the upper frame and to a second end of the lower frame, the actuator comprising a driving motor mounted on the lower frame, wherein the actuator pulls the second end of the upper frame towards the lower frame thereby rotating the second end of the upper frame about the first rotation axis and maintaining a distance between the second end of the upper frame and the first rotation axis and between the frame second ends opposite to the first ends thereof, respectively;

a pressurizing unit which is installed between the first end of the upper frame and the second end of the upper frame; and a mounting unit connected to the lower frame, and mounting the lower frame to an object to be pressurized, wherein the object is pressurized by the pressurizing unit when the actuator rotates the second end of the upper frame toward the object, the lower frame comprises:

a mounting part on which the actuator is mounted, two arms which are parallel to each other and longitudinally extend from the mounting part, a hinge shaft aligned with the first rotation axis, installed at distal ends of the two arms, inserted into the second groove of the upper frame, and an opening having a rectangular shape formed by the mounting part, the two arms and the distal ends of the two arms, and the upper frame is disposed inside the opening formed by the mounting part, the two arms and the distal ends of the two arms when the upper frame is pulled down by the actuator.

2. The pressurizing apparatus of claim 1, wherein the pressurizing unit is installed to and rotatable relative to the upper frame about a second rotation axis which is different from the first rotation axis, wherein the pressurizing unit pressurizes the object by contacting the object according to the rotation of the second end of the upper frame about the first rotation axis.

3. The pressurizing apparatus of claim 2, wherein the pressurizing unit is a fluid bag containing a fluid.

4. The pressurizing apparatus of claim 3, wherein the fluid bag comprises:

a body, an upper fixing frame combined to an upper portion of the body, a lower fixing frame combined to a lower portion of the body, and a rotation shaft combined to the upper frame and aligned with the second rotation axis, such that the rotation shaft protrudes from each of opposing sides of the upper fixing frame, and the pressurizing unit is rotatable relative to the upper frame about the second rotation axis.

5. The pressurizing apparatus of claim 2, wherein the pressurizing unit is disposed inside the opening formed by the mounting part, the two arms and the distal ends of the two arms when the upper frame is pulled down by the actuator.

6. The pressurizing apparatus of claim 2, wherein the second rotation axis is disposed offset by a predetermined interval from a center axis of the pressurizing unit in a direction from the second end of the upper frame toward the first end of the upper frame.

7. The pressurizing apparatus of claim 2, wherein a rotation shaft aligned with the second rotation axis is disposed protruding from each of opposing sides of the pressurizing unit, and a first groove to which the rotation shaft is inserted, is disposed in the upper frame.

8. The pressurizing apparatus of claim 1, wherein a combining shaft which combines the mounting unit to the mounting part, is installed in the mounting part.

9. The pressurizing apparatus of claim 1, wherein a spring is installed between the lower frame and the upper frame, and the spring applies elasticity to the upper frame in a direction where the second end of the upper frame is distanced away from the lower frame.

10. The pressurizing apparatus of claim 1, wherein the actuator further comprises a string connecting the driving motor and the second end of the upper frame.

11. The pressurizing apparatus of claim 1, wherein the driving motor includes a pulley installed on a rotation shaft of the driving motor, and the string is wrapped around the pulley.

12. The pressurizing apparatus of claim 10, wherein the upper frame further includes supporting members disposed on the second end of the upper frame, and a first end of the string is fixed to the lower frame via the supporting members.

13. The pressurizing apparatus of claim 12, wherein the supporting members comprise two supporting rollers spaced apart from each other.

14. The pressurizing apparatus of claim 10, wherein the lower frame includes a guide roller which maintains a direction of the string.

15. The pressurizing apparatus of claim 1, wherein the mounting unit comprises:

a mounting band, wherein each of opposing ends of the mounting band are each connected to each of opposing ends of the lower frame, respectively, and an adhesion unit disposed in a center of the mounting band, which connects distal ends of the mounting band to each other.

16. The pressurizing apparatus of claim 15, wherein the mounting unit further comprises a mounting frame surrounding at least a part of the object, and the lower frame is combined to the mounting frame.

17. The pressurizing apparatus of claim 1, wherein the actuator is connected to the second end of the upper frame at more than one location.

18. The pressurizing apparatus of claim 10, wherein the string is connected to the second end of the upper frame at more than one location.

* * * * *